United States Patent [19]

Sayo et al.

[11] Patent Number: 5,693,868
[45] Date of Patent: Dec. 2, 1997

[54] METHOD FOR PRODUCING OPTICALLY ACTIVE DIPHOSPHINE COMPOUNDS

[75] Inventors: Noboru Sayo; Xiaoyong Zhang; Tatsuya Ohmoto; Akifumi Yoshida; Tohru Yokozawa, all of Kanagawa, Japan

[73] Assignee: Takasago International Corporation, Tokyo, Japan

[21] Appl. No.: 740,506

[22] Filed: Oct. 30, 1996

[30] Foreign Application Priority Data

Oct. 31, 1995 [JP] Japan ................... 7-305211

[51] Int. Cl.$^6$ ................... C07F 9/50; C07F 9/02
[52] U.S. Cl. ................... 568/8; 568/13; 568/14; 568/16; 568/17; 564/15; 549/220
[58] Field of Search ............ 549/220; 564/15; 568/8, 13, 14, 16, 17

[56] References Cited

PUBLICATIONS

Sayo, N et al "Chiral unsymemetric diphosphine compounds and transition metal complexes containing them as ligands" CA 126: 199669 (1997).

*Primary Examiner*—Amelia Owens
*Attorney, Agent, or Firm*—Sughrue, Mion, Zinn, Macpeak & Seas, PLLC

[57] ABSTRACT

The present invention provides a method for producing novel optically active diphosphine compounds [2,2'-bis(di-substituted phosphino)-1,1'-binaphthyl compounds] having a selectivity (chemoselectivity or enantioselectivity) and catalytic activity different from those of conventional BINAP compounds. In a method of the present invention for producing an optically active diphosphine compound (i.e., 2,2-bis(di-substituted phosphino)-1,1'-binaphthyl), 2,2'-bis(trifluoromethanesulfonyloxy)-1,1'-binaphthyl is reacted, in the presence of a transition metal-phosphine complex, with a phosphineoxide compound represented by the following general formula:

$$A_2P(O)H$$

wherein A represents a phenyl group; a mono- to tri-substituted phenyl group, wherein each substituent in the substituted phenyl group is individually selected from the group consisting of a halogen atom, a lower alkyl group, a lower alkoxy group or a lower halogenated-alkoxy group such that one or more of the substituents may be the same or different; a naphthyl group; a lower-alkyl naphthyl group; or a lower-alkoxy naphthyl group.

16 Claims, No Drawings

METHOD FOR PRODUCING OPTICALLY ACTIVE DIPHOSPHINE COMPOUNDS

BACKGROUND OF THE INVENTION

1. Field of the Invention

The present invention relates to a method for producing optically active diphosphine compounds. These compounds are advantageously used as ligands of catalysts for various asymmetric synthesis reactions.

2. Description of the Related Art

Hithereto, many investigations relating to complexes for asymmetric synthesis, for example, transition-metal complexes for asymmetric hydrogenation, asymmetric isomerization, asymmetric hydrosilylation, or the like, have been conducted. Among these, those complexes which comprise an optically active tertiary phosphine compound coordinated with a complex of a transition metal such as ruthenium, rhodium, iridium and palladium generally exhibit excellent performance. Furthermore, many phosphine compounds having a special structure were hithereto developed for further improving performance as described in "Yuuki-Kinzoku-Sakutai no Kagaku" (Chemistry on Organic Metal Complexes) edited by Nihon Kagaku-kai, pp. 237–238, 1982; and Ryoji Noyori, *Asymmetric Catalysis in Organic Synthesis*, published by Wiley-Interscience.

Particularly, 2,2'-bis(diphenylphosphino)-1,1'-binaphthyl (hereinafter, referred to as BINAP) is recognized as an optically active phosphine having excellent properties, and a rhodium complex and a ruthenium complex with BINAP coordinated as a ligand have been reported in Japanese Unexamined Patent Publication Nos. 55-61973 and 61-6390, respectively. Furthermore, a rhodium complex and a ruthenium complex with 2,2'-bis[di-(p-tolyl)phosphino]-1,1'-binaphthyl (hereinafter, referred to as p-TolBINAP) coordinated as a ligand were reported as being effective in asymmetric hydrogenation and asymmetric isomerization in Japanese Unexamined Patent Publication Nos. 60-199898 and 61-63690, respectively. Moreover, a ruthenium complex of 2,2'-bis[di-(3,5-dialkylphenyl)phosphino]-1,1'-binaphthyl was reported as being effective in asymmetric hydrogenation of β-ketoesters in Japanese Unexamined Patent Publication No. 3-25509. However, even when using these phosphine complexes, selectivity (chemoselectivity and enantioselectivity), catalytic activity, and persistency are generally unsatisfactory in some reactions or in reactions using certain kinds of substrates.

The following industrial method is widely known as a conventional method for producing the above-noted phosphine compounds. That is, racemic binaphthol is brominated with triphenylphosphine-dibromide at a high temperature (240°–320° C.). After introducing a Grignard reagent, the resulting product is condensed with diarylphosphinylchloride to produce phosphinedioxide. Then, after optical resolution, the resulting product is transformed into a tertiary phosphine compound (a kind of BINAP compound) with a reductant such as trichlorosilane. This method is described by H. Takaya, K. Mashima, K. Koyano, M. Yagi, H. Kumobayashi, T. Takemori, S. Akutagawa and R. Noyori in *J. Org. Chem.*, vol. 51, p. 629, 1986. Additionally, another method for synthesizing BINAP has been proposed by D. Cai, J. F. Payyach, D. R. Bender, D. L. Hughes, T. R. Verhoeven and P. J. Reider in *J. Org. Chem.*, vol. 59, pp. 7180–7181, 1994 and in the specification of U.S. Pat. No. 5,399,711. In this method, 2,2'-bis(trifluoromethanesulfonyloxy)-1,1'-binaphthyl which is synthesized using an optically active binaphthyl is reacted with diphenylphosphine in the presence of a nickel-phosphine complex to prepare BINAP.

However, each of the above-mentioned methods for producing optically active phosphine compounds has some drawbacks. For example, the former method requires a high temperature to brominate binaphthol, and also requires a special reaction vessel due to generation of hydrobromic acid during bromination. Furthermore, the former method also requires optical resolution of a racemic modification. Therefore, the cost is high when only one of the enantiomorphic isomers is desired. Moreover, many such compounds are difficult to optically resolve. On the other hand, the latter method does not require optically resolving a racemic modification. However, diphenylphosphine, which is used in the latter method, is not suitable for industrial use in large quantities due to its poor stability (diphenylphosphine is easily oxidized), unpleasent odor and toxicity.

On the other hand, since chiral compounds are highly useful, there is a strong demand for an optical phosphine compound which exhibits selectivity (chemoselectivity or enantioselectivity) and which also has a catalytic activity different from conventional BINAP compounds.

SUMMARY OF THE INVENTION

The present inventors conducted extensive investigations to solve the above-mentioned problems of the prior art. As a result, the present inventors obtained the following findings to thereby achieve the present invention. That is, an optically active diphosphine compound (2,2'-bis(di-substituted phosphino)-1,1'-binaphthyl) and/or an optically active diphosphinemonooxide compound (2-di-substituted phosphinyl-2'-di-substituted phosphino-1,1'-binaphthyl) is readily synthesized by reacting 2,2'-bis(trifluoromethanesulfonyloxy)-1,1'-binaphthyl with di-substituted phosphineoxide in the presence of a transition metal-phosphine complex. Furthermore, the optically active diphosphinemonooxide compound is readily reduced to synthesize an optically active diphosphine compound.

Specifically, preferred embodiments of the present invention are as follows.

(1) A method for producing an optically active diphosphine having the following general formula (I):

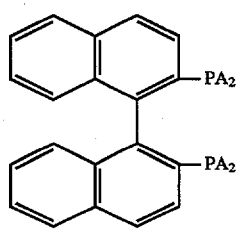

(I)

wherein A represents a phenyl group; a mono- to trisubstituted phenyl group, wherein the substituent of the substituted phenyl group is independently selected from the group consisting of a halogen atom, a lower alkyl group, a lower alkoxy group or a lower halogenated-alkoxy group such that one or more of the substituents may be the same or different; a naphthyl group; a lower-alkyl naphthyl group; or a lower-alkoxy naphthyl group, comprising reacting 2,2'-bis(trifluoromethanesulfonyloxy)-1,1'-binaphthyl represented by the following general formula (II):

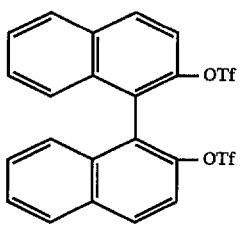

(II)

wherein Tf represents a trifluoromethanesulfonyl group, with a phosphineoxide compound represented by the following general formula (III):

A₂P(O)H  (III)

wherein A has the same meaning as in the above general formula (I), in the presence of a transition metal-phosphine complex.

(2) The method for producing an optically active diphosphine according to the description in (1) above, wherein A in the above general formulae (I) and (III) is selected from the group consisting of a phenyl group, a 4-tolyl group, a 3-tolyl group, a 3,5-xylyl group, a 3,4,5-trimethylphenyl group, a 4-methoxyphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-tert-butylphenyl group, a 3,5-di-tert-butylphenyl group, a 4-chlorophenyl group, a 4-fluorophenyl group, a 4-trifluoromethylphenyl group, a 3-trifluoromethylphenyl group, a 4-dimethylaminophenyl group, a 4-biphenyl group, a 3-biphenyl group, an α-naphthyl group, a β-naphthyl group, a 6-methoxy-α-naphthyl group and a 6-methoxy-β-naphthyl group.

(3) The method for producing an optically active diphosphine according to the description in (1) or (2) above, wherein the metal of the transition metal-phosphine complex is selected from the group consisting of copper, iron, cobalt, nickel and palladium.

The optically active 2,2'-bis(di-substituted phosphino)-1,1'-binaphthyl of the present invention can be synthesized, for example, according to the following reaction scheme.

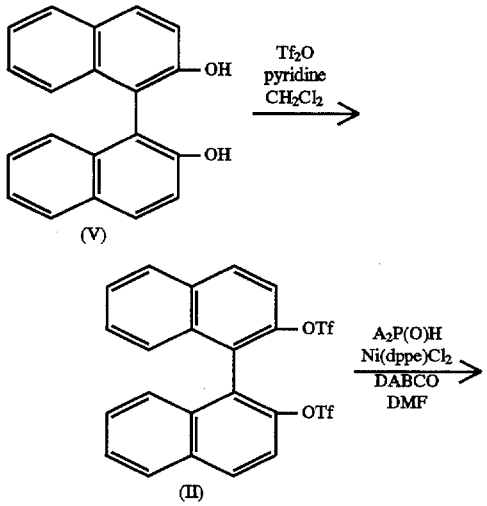

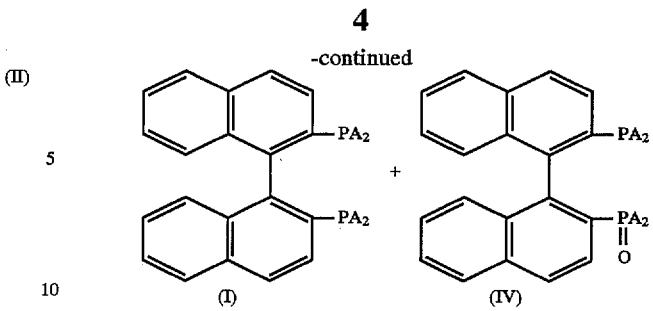

Specifically, an optically active binaphthol (V) is converted into 2,2'-bis(trifluoromethanesulfonyloxy)-1,1'-binaphthyl (II) by any of the methods described in M. Vondenhof and J. Mattay, Tetrahedron Lett., vol. 31, pp. 985–988, 1990; L. Kurz, G. Lee, D. Morgans, Jr., M. J. Waldyke and T. Ward, Tetrahedron Lett., vol. 31, pp. 6321–6324, 1990; and Y. Uozumi, A. Tanahashi, S. Y. Lee and T. Hayashi, J. Org. Chem., vol. 58, pp. 1945–1948, 1993. Subsequently, the resulting product is reacted with a di-substituted phosphineoxide (III) in the presence of a catalytic amount of a transition metal-phosphine complex to synthesize a mixture which contains an optically active diphosphine compound (2,2'-bis(di-substituted phosphino)-1,1'-binaphthyl) (I) and/or an optically active diphosphinemonooxide compound (2-di-substituted phosphinyl-2'-di-substituted phosphino-1,1'-binaphthyl) (IV). Additionally, the above optically active diphosphinemonooxide compound (IV) is readily transformed into the optically active diphosphine compound (I) by reduction.

In practice, as typically shown in Example 1-(2) below, a mixture which principally contains (S)-2-di(2-naphthyl)phosphinyl-2'-di(2-naphthyl)phosphino -1,1'-binaphthyl as the optically active diphosphinemonooxide compound (IV) can be synthesized using di(2-naphthyl)phosphineoxide as the di-substituted phosphine oxide (III).

Furthermore, as typically shown in Example 1-(4) below, a mixture which principally contains (R)-2,2'-bis[di(4-trifluoromethylphenyl)phosphino]-1,1'-binaphthyl as the optically active diphosphine compound (I) can be synthesized using di(4-trifluoromethylphenyl)phosphineoxide as the di-substituted phosphine oxide (III).

Moreover, as typically shown in Example 2 below, a mixture which principally contains (R)-2-diphenylphosphinyl-2'-diphenylphosphino-1,1'-binaphthyl as the optically active diphosphinemonooxide compound (IV) and (R)-2,2'-bis(diphenylphosphino)-1,1'-binaphthyl as the optically active diphosphine compound (I) can be synthesized using diphenylphosphineoxide as the di-substituted phosphine oxide (III).

The functional group A in a di-substituted phosphineoxide (III) used in the above reaction is a phenyl group; a mono- to tri-substituted phenyl group, wherein the substituent of the substituted phenyl group is independently selected from the group consisting of a halogen atom, a lower alkyl group, a lower alkoxy group or a lower halogenated-alkoxy group such that one or more of the substituents may be the same or different; a naphthyl group; a lower-alkyl naphthyl group; or a lower-alkoxy naphthyl group. As used herein, the term "lower" means a group having from 1 to 4 carbon atoms.

Typical examples of the functional group A include a phenyl group, a 4-tolyl group, a 3-tolyl group, a 3,5-xylyl group, a 3,4,5-trimethylphenyl group, a 4-methoxyphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-tert-butylphenyl group, a 3,5-di-tert-butylphenyl group, a 4-chlorophenyl group, a 4-fluorophenyl group, a 4-trifluoromethylphenyl group, a 3-trifluoromethylphenyl group, a 4-dimethylaminophenyl group, a 4-biphenyl group, a 3-biphenyl group, an α-naphthyl group, a β-naphthyl group, a 6-methoxy-α-naphthyl group and a 6-methoxy-β-naphthyl group.

The substituted phosphineoxide should be used in a mole equivalent weight of from 2 to 5 times, and preferably, from 3 to 4 times the amount of ditrifluoromethanesulfonyloxy binaphthyl (triflate).

The di-substituted phosphineoxide (III) is preferably recrystallized or purified with a silica gel column before use.

The di-substituted phosphineoxide (III) can be synthesized following the methods described by B. B. Hunt, B. C. Saunders, et al. in *J. Chem. Soc.*, pp. 2413–2414, 1957 and by H. R. Hays, et al. in *J. Org. Chem.*, vol. 33, pp. 3690–3694, 1968. Specifically, a Grignard reagent represented by AX is reacted with diethyl phosphite. The reaction scheme is shown below.

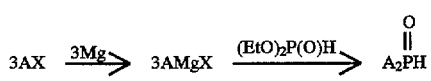

$$3AX \xrightarrow{3Mg} 3AMgX \xrightarrow{(EtO)_2P(O)H} A_2\overset{O}{\overset{\|}{P}}H$$

The transition metal-phosphine complex of the present invention which is used in the above reaction in a catalytic amount may include a complex coordinated with copper, iron, cobalt, nickel, palladium, or the like. Typical examples of the transition metal-phosphine complex are as follows. In the list of examples below, the abbreviation Me indicates methyl, Ph indicates phenyl, dppe indicates 1,2-bis (diphenylphosphino)ethane, dppp indicates 1,3-bis (diphenylphosphino)propane, and dppb indicated 1,4-bis (diphenylphosphino)butane.

Cu: CuMe(PPh₃)₃, Cu(Me)₂(dppe), CuCl(PPh₃)₃

Fe: Fe(Co)₂(PPh₃)₃, FeCl₂(PPh₃)₂, FeCl₂(dppe), FeHCl (dppe), FeCl₃(PPh₃)₃, FeCl₂(dppp), FeCl₂(dppb)

Co: CoCl(PPh₃)₃, CoCl₂(dppe), CoCl₂(dppp), CoCl₂(dppb)

Ni: Ni(PPh₃)₄, Ni(PPh₃)₂, NiCl₂(dppe), NiCl₂(dppp), NiCl₂(dppb)

Pd: PdCl₂(PPh₃)₂, PdCl₂(dppe), PdCl₂(dppp), PdCl₂(dppb)

Examples of the base for use in the reaction of the present invention include 1,4-diazabicyclo[2.2.2]octane (DABCO), diazabicycloundecene (DBU), tetramethylethylenediamine (TMEDA), dimethylaniline, 1,4-dimethylpiperazine, 1-methylpiperidine, 1-methylpyrrolidine, quinuclidine, 1-methylmorpholine, triethylamine, diisopropylethylamine and 1-methyl-2,2,6,6-tetramethylpiperidine.

Furthermore, examples of the solvent for use in the reaction of the present invention include N,N-dimethylformamide (DMF), dimethylsulfoxide (DMSO), N-methylpyrrolidone (NMP) and dimethylacetamide (DMA).

The reaction temperature is generally from 80° to 140° C., and preferably from 100° to 120° C.

In the reaction conditions described above, a mixture containing an optically active diphosphine compound [2,2'-bis(di-substituted phosphino)-1,1'-binaphthyl] (I) and/or an optically active diphosphinemonooxide compound [2-di-substituted phosphinyl-2'-di-substituted phosphino-1,1'-binaphthyl] (IV) is readily produced from 2,2'-bis (trifluoromethanesulfonyloxy)-1,1'-binaphthyl (II).

Furthermore, the diphosphinemonooxide compound [2-di-substituted phosphinyl-2'-di-substituted phosphino-1, 1'-binaphthyl] (IV) or a mixture containing the same, after purification or directly, can be reduced to an optically active diphosphine compound as the objective product, i.e., a 2,2'-bis(di-substituted phosphino)-1,1'-binaphthyl derivative (I), with a reductant such as trichlorosilane according to the reaction scheme below.

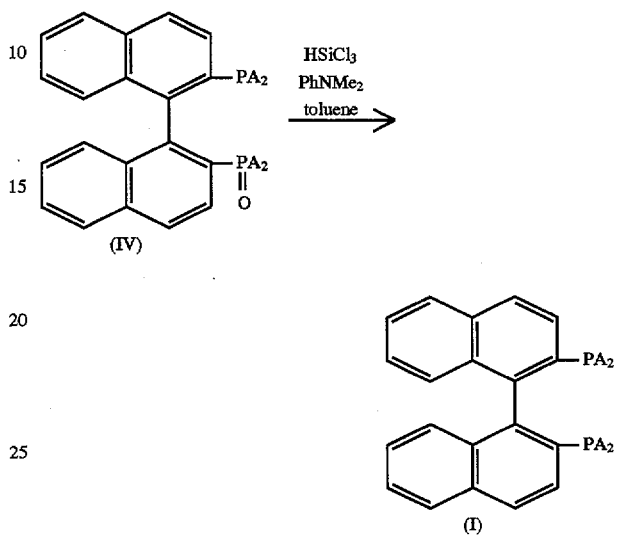

Moreover, in the present invention, among the optically active diphosphine compounds (2,2'-di-substituted phosphino-1,1'-binaphthyl compounds) expressed by general formula (I), those compounds where A represents a 3,4,5-trimethylphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-fluorophenyl group, a 4-trifluoromethylphenyl group, a 3-trifluoromethylphenyl group, a 4-biphenyl group, a 3-biphenyl group, a 4-dimethylaminophenyl group, an α-naphthyl group, a β-naphthyl group, a 6-methoxy-α-naphthyl group, a 6-methoxy-β-naphthyl group, or the like, respectively, are novel compounds.

Some examples of A are given below as follows.

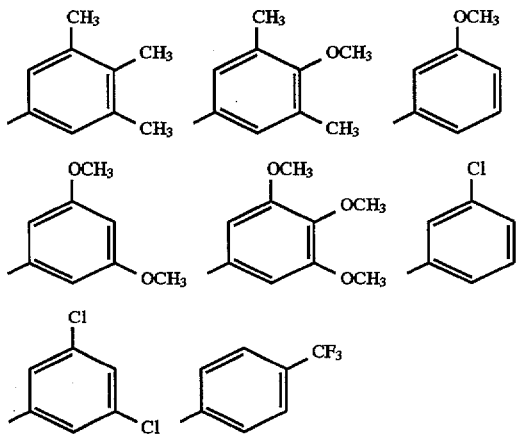

-continued

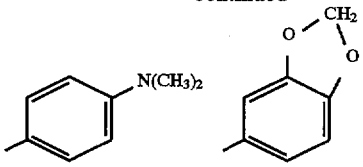

The above-identified novel compounds obtained by the aforementioned method form complexes with transition metals as described below. Such complexes with transition metals are advantageously used as catalysts for asymmetric synthesis.

Furthermore, in the present invention, among the optically active diphosphinemonooxide compounds (2-di-substituted phosphinyl-2'-di-substituted phosphino-1,1'-binaphthyl compounds) expressed by general formula (IV), all of these compounds are novel except for the compound where A is a phenyl group.

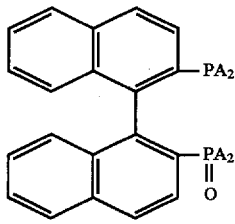
(IV)

In the above general formula (IV), A represents a phenyl group; a mono- to tri-substituted phenyl group, wherein the substituent in the substituted phenyl group is independently selected from a halogen atom, a lower alkyl group, a lower alkoxy group or a lower halogenated-alkoxy group such that one or more of the substituents may be the same or different; a naphthyl group; a lower-alkyl naphthyl group; or a lower-alkoxy naphthyl group.

These novel compounds, which can be obtained by the aforementioned method, are advantageously used as intermediates of transition-metal complexes which in turn are useful as catalysts for asymmetric synthesis as described below.

2,2'-bis(di-substituted phosphino)-1,1'-binaphthyl (I) which is obtained according to the present invention can be a ligand which forms a complex with a transition metal.

Examples of the transition metal include rhodium, ruthenium, iridium, palladium and nickel.

For preparing such transition-metal complexes, known methods such as those described below can be employed. Regarding the abbreviations used in the general formulae of various transition-metal complexes described below, L indicates the diphosphine compound represented by general formula (I), cod indicates 1,5-cyclooctadiene, nbd indicates norbornadiene, Ph indicates a phenyl group, and Ac indicates an acetyl group. Rhodium complex:

According to the method described in Jikken-Kagaku Kouza (Experimental Chemistry), 4th edition, vol. 18, "Yuuki-Kinzoku-Sakutai" (Organometallic Complex), pp. 339–344 (1991) edited by Nihon Kagaku-kai and published by Maruzen Co., a rhodium complex can be prepared by reacting 2,2'-bis(di-substituted phosphino)-1,1'-binaphthyl (I) of the present invention with bis(cycloocta-1,5-diene) rhodium(I)tetrafluoroborate.

The following are practical examples of such rhodium complexes.

Rh(L)Cl, Rh(L)Br, Rh(L)I, [Rh(cod)(L)]BF$_4$, [Rh(cod)(L)]ClO$_4$, [Rh(cod)(L)]PF$_6$, [Rh(cod)(L)]BPh$_4$, [Rh(nbd)(L)]BF$_4$, [Rh(nbd)(L)]ClO$_4$, [Rh(nbd)(L)]PF$_6$, [Rh(nbd)(L)]BPh$_4$ Ruthenium complex: According to the method described in "J. Chem. Soc.", Chem. Commun., p. 922 (1988), a ruthenium complex can be produced by heat-refluxing 2,2'-bis(di-substituted phosphino)-1,1'-binaphthyl (I) and [Ru(cod)Cl$_2$]$_n$ in the presence of triethylamine in a toluene solvent. Alternatively, according to the method described in "J. Chem. Soc.", Chem. Commun., p. 1208 (1989), a ruthenium complex can be produced by heating and stirring 2,2'-bis(di-substituted phosphino)-1,1'-binaphthyl (I) and [Ru(p-cymene)I$_2$]$_2$ together with methylene chloride and ethanol.

The following are practical examples of such ruthenium complexes.

Ru(OAc)$_2$(L), Ru$_2$Cl$_4$(L)$_2$N(C$_2$H$_5$)$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [RU(L)](BF$_4$)$_2$, [Ru(L)](ClO$_4$)$_2$, [RU(L)](PF$_6$)$_2$, [Ru(L)](BPh$_4$)$_2$ Iridium complex:

According to the method described in J. Organomet. Chem., vol. 428, p. 213 (1992), a iridium complex can be produced by reacting 2,2'-bis(di-substituted phosphino)-1,1'-binaphthyl (I) and [Ir(cod)(CH$_3$CN)$_2$]BF$_4$ in tetrahydrofuran while stirring.

The following are practical examples of such iridium complexes.

Ir(L)Cl, Ir(L)Br, Ir(L)I, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]BF$_4$, [Ir(nbd)(L)]ClO$_4$, [Ir(nbd)(L)]PF$_6$, [Ir(nbd)(L)]BPh$_4$ Palladium complex:

According to the method described in J. Am. Chem. Soc., vol. 113, p. 9887 (1991), a palladium complex can be produced by reacting 2,2'-bis(di-substituted phosphino)-1,1'-binaphthyl (I) and π-allylpalladiumchloride.

The following are practical examples of such palladium complexes.

PdCl$_2$(L), (π-allyl)Pd(L), [Pd(L)]BF$_4$, [Pd(L)]ClO$_4$, [Pd(L)]PF$_6$, [Pd(L)]BPh$_4$ Nickel complex:

According to the method described in Jikken-Kagaku Kouza (Experimental Chemistry), 4th edition, vol. 18, "Yuuki-Kinzoku-Sakutai" (Organometallic Complex), p. 376 (1991) edited by Nihon Kagaku-kai and published by Maruzen Co., a nickel complex is produced by heating and stirring 2,2'-bis(di-substituted phosphino)-1,1'-binaphthyl (I) and nickel chloride which are dissolved in a mixture of isopropanol and methanol.

The following are practical examples of such nickel complexes.

NiCl$_2$(L), NiBr$_2$(L), NiI$_2$(L)

According to the present invention, a method is provided for producing a low-cost, optically active diphosphine compound [2,2'-bis(di-substituted phosphino)-1,1'-binaphthyl] using optically active binaphthol as a raw material. In addition, according to the present invention, an optically active diphosphine compound can be obtained by once synthesizing a novel diphosphinemonooxide compound (2-di-substituted phosphinyl-2'-di-substituted phosphino-1,1'-binaphthyl) and subsequently reducing the novel compound.

A transition-metal complex which can be synthesized from an optically active phosphine compound can provide the objective product in high yield, and particularly, with high enantioselectivity when used as a catalyst in asymmetric synthesis, and more specifically, in a reaction such as asymmetric hydrogenation and asymmetric hydrosilylation. Furthermore, an objective product having the desired absolute configuration can be obtained in an asymmetric synthesis reaction by using, as a catalyst, a transition-metal complex which has a ligand selected from either the (−) and (+) isomers of the ligands of the present invention.

DESCRIPTION OF THE PREFERRED EMBODIMENTS

According to the present invention, a mixture containing an optically active diphosphine compound [2,2'-bis(disubstituted phosphino)-1,1'-binaphthyl] (I) and/or an optically active diphosphinemonooxide compound (2-disubstituted phosphinyl-2'-di-substituted phosphino-1,1'-binaphthyl) (IV) is produced by reacting 2,2'-bis(trifluoromethanesulfonyloxy)-1,1'-binaphthyl represented by the following general formula

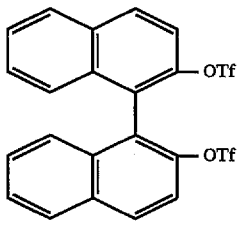

(II)

wherein Tf represents a trifluoromethanesulfonyl group, with a phosphineoxide compound represented by the following general formula (III):

(III)

wherein A is selected from the group consisting of a phenyl group, a 4-tolyl group, a 3-tolyl group, a 3,5-xylyl group, a 3,4,5-trimethylphenyl group, a 4-methoxyphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-tert-butylphenyl group, a 3,5-di-tert-butylphenyl group, a 4-chlorophenyl group, a 4-fluorophenyl group, a 4-trifluoromethylphenyl group, a 3-trifluoromethylphenyl group, a 4-dimethylaminophenyl group, a 4-biphenyl group, a 3-biphenyl group, an α-naphthyl group, a β-naphthyl group, a 6-methoxy-α-naphthyl group and a 6-methoxy-β-naphthyl group, in the presence of a transition metal-phosphine complex.

The above mixture containing the optically active diphosphine compound and/or an optically active diphosphinemonooxide compound is purified or further reduced with a reductant such as trichlorosilane to produce an optically active diphosphine compound represented by general formula (I):

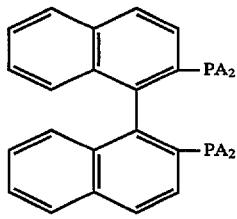

(I)

wherein A is selected from the group consisting of a phenyl group, a 4-tolyl group, a 3-tolyl group, a 3,5-xylyl group, a 3,4,5-trimethylphenyl group, a 4-methoxyphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-tert-butylphenyl group, a 3,5-di-tert-butylphenyl group, a 4-chlorophenyl group, a 4-fluorophenyl group, a 4-trifluoromethylphenyl group, a 3-trifluoromethylphenyl group, a 4-dimethylaminophenyl group, a 4-biphenyl group, a 3-biphenyl group, an α-naphthyl group, a β-naphthyl group, a 6-methoxy-α-naphthyl group and a 6-methoxy-β-naphthyl group.

The optically active diphosphine compounds obtained by the above-described method can form complexes with transition metals. Such transition-metal complexes are advantageously used as catalysts for asymmetric synthesis.

The present invention will be further illustrated with the following Examples, which are not to be construed as limiting the scope of the present invention.

The following are the apparatuses which were used to measure the physico-chemical properties of the products obtained in each of the Examples below.

$^1$H NMR: Bruker AM400 (400 MHz)
$^{31}$NMR: Bruker AM400 (162 MHz)
Melting Point (mp): Yanaco MP-500D
Optical Rotation: Nihon Bunkou DIP-4
GLC: HEWLETT Packard 5890-II
HPLC: Shimazu LC10AT and SPD10A
MASS: Hitachi M-80B

EXAMPLE 1

(1) Synthesis of (S)-2,2'-bis(trifluoromethanesulfonyloxy)-1,1'-binaphthyl 36.2 g (127 mmol) of (S)-binaphthol and 25.2 g (319 mmol) of pyridine were dissolved in 181 ml of methylene chloride and cooled to 0° C. To this mixture, 76.5 ml (271 mmol) of triflic anhydride (trifluoromethanesulfonic anhydride) was dropwise added and then stirred for 18 hours at room temperature. To the reaction mixture thus obtained, 200 ml of a 2 N hydrochloric acid solution was added for washing. The organic layer was washed with water and with a sodium chloride solution. Subsequently, the solvent was removed by distillation to obtain 69.3 g of a crude product. This crude product was then dissolved in 280 ml of hexane and recrystallized to obtain 64.1 g (yield 92%) of the objective compound. The physico-chemical property of the product thus obtained was measured as follows.

$^1$H NMR (CDCl$_3$) δ7.25–8.15 (m, ArH)

(2) Synthesis of (S)-2-di(2-naphthyl)phosphinyl-2'-di(2-naphthyl)phosphin o-1,1'-binaphthyl 19.92 g (36.2 mmol) of (S)-2,2'-bis(trifluoromethanesulfonyloxy)-1,1'-binaphthyl, 3.82 g (7.2 mmol) of NiCl$_2$ (dppe), and 11.8 g (119.4 mmol) of N-methylpiperidine were dissolved in 80 ml of DMF and stirred for 15 min. at room temperature and for another 15 min. at 100° C. To this mixture, 41.6 g (137.5 mmol) of di(2-naphthyl)phosphineoxide dissolved in 100 ml of DMF was added thereto and stirred for 24 hours at 100° C. The reaction mixture thus obtained was cooled to room temperature. After the solvent was removed by distillation, 75 ml of methylene chloride was added to the residue. The resultant solution was cooled in an ice water bath, and 240 ml of a 1 N hydrochloric acid solution was gradually added thereto dropwise, and stirred at room temperature for 24 min. After separating the liquid layers, the aqueous layer was extracted with methylene chloride. The resultant organic layer was recovered and washed with water, and dried with magnesium sulfate. After decreasing the solvent content, the concentrate was purified by silica gel chromatography (hexane:ethyl acetate=4:1 to 1:4) to obtain 40.0 g (yield 40%) of the objective compound as yellowish white crystals. The physico-chemical properties of the product thus obtained were measured as follows.

mp 285° to 287° C.

$[\alpha]_D^{24}$ −51.4° (c 1.08, CHCl$_3$)

$^1$H NMR (CDCl$_3$) δ6.45 to 8.17 (m, ArH)

$^{31}$P NMR (CDCl$_3$) δ−13.05(S) 28.28(s)

CI-Mass spectrum m/z 840 (M$^+$+H+1)

(3) Synthesis of (S)-2,2'-bis[di(2-naphthyl)phosphino]-1,1'-binaphthyl 15.04 g (17.9 mmol) of (S)-2-di(2-naphthyl)phosphinyl-2'-di(2-naphthyl)phosphino-1,1'-binaphthyl and 12.5 g (103 mmol) of dimethylaniline were dissolved in 270 ml of toluene. To this solution, 14.1 g (104 mmol) of trichlorosilane was added, and stirred at 90° C. for 1 hour and for 28 hours while refluxing. The reaction mixture thus obtained was cooled in an ice water bath, and 120 ml of a 20% NaOH solution was added thereto. The resultant aqueous layer was extracted with toluene. The thus obtained organic layer was then washed with 50 ml of water, with 10 ml of a 2 N hydrochloric acid solution, and with 50 ml of water. After concentration, the resultant solution was purified by silica gel chromatography (hexane:ethyl acetate=1:0 to 1:1) to obtain 14.9 g (yield 87%) of the objective compound as a white solid. The physico-chemical properties of the product were measured as follows.

mp 291° to 293° C.

$[\alpha]_D^{24}$ −132.2° (C 0.99, CHCl$_3$)

$^{31}$P NMR (CDCl$_3$) δ−13.57(S)

CI-Mass spectrum m/z (M$^+$+H+1)

(4) Synthesis of (R)-2,2'-bis[di(4-trifluoromethylphenyl)phosphino]-1,1'-binaphthyl 1.01 g (1.83 mmol) of (R)-2,2'-bis(trifluoromethanesulfonyloxy)-1,1'-binaphthy 1, 97 mg (0.18 mmol) of NiCl$_2$ (dppe), 2.48 g (7.33 mmol) of di(4-trifluoromethylphenyl)phosphineoxide and 457 mg (4.1 mmol) of DABCO were dissolved in 10 ml of DMF and stirred at 100° C. for 48 hours. The reaction mixture thus obtained was concentrated, 30 ml of methylene chloride was added thereto, and the thus treated reaction mixture was then washed with water. The resultant was further washed with 10 ml of a 5% hydrochloric acid solution and with a saturated sodium chloride solution, and subsequently, dried with magnesium sulfate. After decreasing the solvent content, the concentrate was purified by silica gel chromatography (hexane:ethyl acetate=4:1 to 1:4) to obtain 0.57 g (yield 34%) of the objective compound as yellowish white crystals. The physico-chemical properties of the product were measured as follows.

mp 62° to 64° C.

$[\alpha]_D^{25}$ +3.57° (c 0.50, CHCl$_3$)

$^{31}$P NMR (CDCl$_3$) δ5.4

CI-Mass spectrum m/z 912 (M$^+$)

EXAMPLE 2

(1) Synthesis of (R)-2-diphenylphosphinyl-2'-diphenylphosphino-1,1'-binaphthyl 2.05 g (3.7 mmol) of (S)-2,2'-bis(trifluoromethanesulfonyloxy)-1,1'-binaphthyl, 0.20 g (0.37 mmol) of NiCl$_2$ (dppe), 2.89 g (13.3 mmol) of diphenylphosphineoxide and 1.13 g (11.4 mmol) of N-methylpiperidine were dissolved in 16 ml of DMF and stirred at 100° C. for 39 hours. The reaction mixture thus obtained was cooled to room temperature. After the solvent was removed by distillation, 20 ml of methylene chloride was added to the residue. The resultant solution was cooled in an ice water bath, and 100 ml of a 2 N hydrochloric acid solution was gradually added thereto dropwise, and stirred at room temperature for 30 min. After separating the liquid layers, the aqueous layer was extracted with methylene chloride. The resultant organic layer was recovered and washed with water, and dried with magnesium sulfate. After decreasing the solvent content, the concentrate was purified by silica gel chromatography (hexane:ethyl acetate=4:1 to 1:4) to obtain 0.83 g (yield 35%) of the objective compound as yellowish white crystals. The physico-chemical properties of the product were measured as follows.

mp 236° to 238° C.

$[\alpha]_D^{25}$ +97.5° (c 0.82, CHCl$_3$)

$^1$H NMR (CDCl$_3$) δ6.65 to 7.91 (m, ArH)

$^{31}$P NMR (CDCl$_3$) δ−14.55(S) 27.74(S)

CI-Mass spectrum m/z 622 (M$^+$)

(2) Synthesis of (R)-2,2'-bis(diphenylphosphino)-1,1'-binaphthyl 0.95 ml (9.4 mmol) of trichlorosilane was added to a mixture comprising 1.5 g (2.35 mmol) of (R)-2-diphenylphosphinyl-2'-diphenylphosphino-1,1'-binaphthyl, 4.8 ml (4.4 mmol) of dimethylaniline and 30 ml of toluene. The resultant mixture was then stirred at 90° C. for 1 hour and for 16 hours while refluxing. The reaction mixture thus obtained was cooled in an ice water bath, and 20 ml of a 3 N NaOH solution was added thereto. The resultant aqueous layer was extracted with toluene. The thus obtained organic layer was then washed with 10 ml of water, with 20 ml of a 1 N hydrochloric acid solution, and with 10 ml of water. After concentration, the resultant solution was purified by silica gel chromatography (hexane:ethyl acetate=1:0 to 1:1) to obtain 1.34 g (yield 92%) of the objective compound as a white solid. The physico-chemical properties of the product were measured as follows.

mp 241° to 242° C.

$[\alpha]_D^{24}$ −228° (c 0.68, benzene)

$^{31}$P NMR (CDCl$_3$) δ−12.8(s)

CI-Mass spectrum m/z 622 (M$^+$)

EXAMPLE S3-5

Following the procedure in the above Examples 1 and 2, several diphosphinemonooxide compounds (I) were prepared. The compounds thus obtained are listed in Table 1 below.

TABLE 1

| Example No. | A | Physico-Chemical Properties |
|---|---|---|
| 3 | 4-fluorophenyl | mp: 120 to 125° C.<br>$[\alpha]_D^{25}$: +54.1° (c 0.32, CHCl$_3$)<br>$^{31}$P NMR(CDCl$_3$)δ −16.8, 26.2<br>CI—MS: 711(M$^+$ + H) |
| 4 | 3,5-dimethoxyphenyl | mp: 104 to 107° C.<br>$[\alpha]_D^{25}$: +56.5° (c 0.32, CHCl$_3$)<br>$^{31}$P NMR(CDCl$_3$)δ −10.6, 28.9<br>CI—MS: 880(M$^+$ + H-1) |
| 5 | 3,4-methylenedioxyphenyl | mp: 158 to 159° C.<br>$[\alpha]_D^{25}$: −37.49° (c 1.06, CHCl$_3$)<br>$^{31}$P NMR(CDCl$_3$)δ −10.7, −1.7<br>CI—MS: 815(M$^+$ + H) |

EXAMPLES 6–8

Following the procedure in the above Examples 1 and 2, several diphosphine compounds (I) were prepared. The compounds thus obtained are listed in Table 2 below.

TABLE 2

| Example No. | A | Physico-Chemical Properties |
|---|---|---|
| 6 | 4-fluorophenyl | mp: 213° C.<br>$[\alpha]_D^{25}$: +92.5° (c 0.50, CHCl$_3$)<br>$^{31}$P NMR(CDCl$_3$)δ −16.6<br>CI—MS: 695(M$^+$ + H) |
| 7 | 3,5-dimethoxy-phenyl | mp: 89 to 94° C.<br>$[\alpha]_D^{25}$: +131.1° (c 0.51, CHCl$_3$)<br>$^{31}$P NMR(CDCl$_3$)δ −10.9<br>CI—MS: 863(M$^+$ + H-1) |
| 8 | 3,4-methylene-dioxyphenyl | mp: 119 to 120° C.<br>$[\alpha]_D^{25}$: −13.2° (c 1.03, CHCl$_3$)<br>$^{31}$P NMR(CDCl$_3$)δ −12.1<br>CI—MS: 815(M$^+$ + H) |

Reference EXAMPLE S1–5

Synthesis of Ruthenium Complexes and Rhodium Complexes

Ruthenium complexes and rhodium complexes were prepared using the diphosphine compounds obtained in Examples 2 and 6–8 as ligands.

Each Ruthenium complex was prepared as follows.

48.9 mg (0.05 mmol) of [Ru(p-cymene)I$_2$]$_2$ and 0.1 mmol of a ligand were dissolved in a mixed solution comprising 6 ml of methylene chloride and 3 ml of EtOH, and stirred at 50° C. for 3 hours. After removing the solvent, the resultant solid was analyzed by NMR.

Meanwhile, each rhodium complex was produced as follows.

40.5 mg (0.1 mmol) of [Rh(cod)$_2$]BF$_4$ and 0.1 mmol of a ligand were dissolved in a mixed solution comprising 5 ml of THF and 5 ml of methylene chloride, and stirred at room temperature for 2 hours. After removing the solvent, the resultant solid was analyzed by NMR.

The results of the above analyses are shown in Table 3 below.

TABLE 3

| Reference Example No. | A | Ruthenium Complex | Rhodium Complex |
|---|---|---|---|
| 1 | naphthyl | [RuI(p-cymene)(L)]I<br>$^{31}$P NMR(CDCl$_3$)δ<br>26.17(d, J=60Hz)<br>41.69(d, J=60Hz) | [Rh(cod)(L)]BF4<br>$^{31}$P NMR (CDCl$_3$)δ<br>27.18(d, J=145.9Hz) |
| 3 | 4-fluorophenyl | [RuI(p-cymene)(L)]I<br>$^{31}$P NMR(CDCl$_3$)δ<br>23.5(d, J=60Hz)<br>39.3(d, J=60Hz) | [Rh(cod)(L)]BF4<br>$^{31}$P NMR(CDCl$_3$)δ<br>24.65(d, J=145.9Hz) |
| 4 | 3,5-dimethoxy-phenyl | [RuI(p-cymene)(L)]I<br>$^{31}$P NMR(CDCl$_3$)δ<br>28.1(d, J=58.2Hz)<br>43.9(d, J=58.3Hz) | [Rh(cod)(L)]BF4<br>$^{31}$P NMR(CDCl$_3$)δ<br>29.35(d, J=145.9Hz) |
| 5 | 3,4-methylene-dioxyphenyl | [RuI(p-cymene)(L)]I<br>$^{31}$P NMR(CDCl$_3$)δ<br>26.6(d, J=52.5Hz)<br>41.9(d, J=59.8Hz) | [Rh(cod)(L)]BF4<br>$^{31}$P NMR(CDCl$_3$)δ<br>27.55(d, J=147.7Hz) |

Reference Example 6

Methyl 2-benzamidemethyl-3-oxobutyrate was hydrogenated using a ruthenium complex with a diphosphine compound as a ligand.

13 mg (0.01 mmol) of [RuI(p-cymene)(3,4-methylenedioxyphenyl-BINAP)] synthesized in Reference Example 5, 2.49 g (10 mmol) of methyl 2-benzamidemethyl-3-oxobutyrate, 8.7 ml of methylene chloride, and 1.2 ml of methanol were placed in an autoclave having a volume of 100 ml, and reacted at 60° C. for 21 hours under a hydrogen pressure of 50 atm.

HPLC analysis (column: COSMOSIL 5C-18AR, 4.6×250 mm; solution: MeCN/H$_2$O=30/70; flow rate: 1 ml/min; detection wavelength: 254 nm) demonstrated that syn-alcohol and anti-alcohol were produced in a ratio of 87:13, respectively. Furthermore, the optical purity of the hydrogenation product was measured as follows: 25 mg of the hydrogenation product, 75 mg of (S)-α-methoxy-α-trifluoromethylphenylacetylchloride and 0.5 ml of pyridine were mixed together and stirred. The thus produced (S)-α-methoxy-α-trifluoromethylacetate was analyzed by HPLC (column: COSMOSIL 5SL, 4.6×250 mm; solution: hexane/THF/methanol=1000/100/1; flow rate: 1 ml/min; detection wavelength: 254 nm). The optical purity value was 99% e.e. in terms of the syn-alcohol.

While the invention has been described in detail and with reference to specific embodiments thereof, it will be apparent to one skilled in the art that various changes and modifications can be made therein without departing from the spirit and scope thereof.

We claim:

1. A method for producing an optically active 2 diphosphine having the following general formula (I):

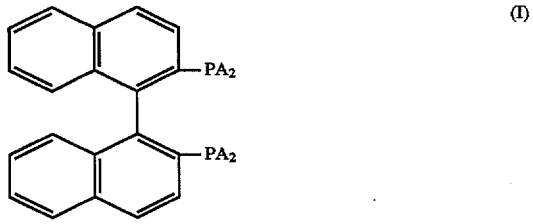

(I)

wherein A represents a phenyl group; a mono- to tri-substituted phenyl group, wherein each substituent of the substituted phenyl group is selected from the group consisting of a halogen atom, a lower alkyl group, a lower alkoxy group or a lower halogenated-alkoxy group such that the substituents may be the same or different; a naphthyl group; a lower-alkyl naphthyl group; or a lower-alkoxy-naphthyl group, comprising reacting 2,2'-bis(trifluoromethanesulfonyloxy)-1,1'-binaphthyl represented by the following general formula (II):

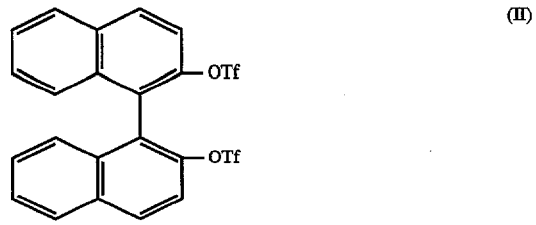

(II)

wherein Tf represents a trifluoromethanesulfonyl group, with a phosphineoxide compound represented by the following general formula (III):

A$_2$P(O)H    (III)

wherein A has the same meaning as in the above general formula (I), in the presence of a transition metal-phosphine complex.

2. The method for producing an optically active diphosphine according to claim 1, wherein A in general formulae (I) and (III) is selected from the group consisting of a phenyl group, a 4-tolyl group, a 3-tolyl group, a 3,5-xylyl group, a 3,4,5-trimethylphenyl group, a 4-methoxyphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-tert-butylphenyl group, a 3,5-di-tert-butylphenyl group, a 4-chlorophenyl group, a 4-fluorophenyl group, a 4-trifluoromethylphenyl group, a 3-trifluoromethylphenyl group, a 4-dimethylaminophenyl group, a 4-biphenyl group, a 3-biphenyl group, an α-naphthyl group, a β-naphthyl group, a 6-methoxy-α-naphthyl group and a 6-methoxy-β-naphthyl group.

3. The method for producing an optically active diphosphine according to claim 1, wherein the metal of the transition metal-phosphine complex is selected from the group consisting of copper, iron, cobalt, nickel and palladium.

4. The method for producing an optically active diphosphine according to claim 2, wherein the metal of the transition metal-phosphine complex is selected from the group consisting of copper, iron, cobalt, nickel and palladium.

5. The method for producing an optically active diphosphine according to claim 1, wherein the phosphineoxide compound represented by general formula (III) is used in a mole equivalent weight of from 2 to 5 times the amount of the 2,2'-bis(trifluoromethanesulfonyloxy)-1,1'-binaphthyl represented by general formula (II).

6. The method for producing an optically active diphosphine according to claim 2, wherein the phosphineoxide compound represented by general formula (III) is used in a mole equivalent weight of from 2 to 5 times the amount of the 2,2'-bis(trifluoromethanesulfonyloxy)-1,1'-binaphthyl represented by general formula (II).

7. The method for producing an optically active diphosphine according to claim 1, comprising reacting a compound represented by general formula (II) with a compound represented by general formula (III) in the presence of a transition metal-phosphine complex and a base.

8. The method for producing an optically active diphosphine according to claim 2,. comprising reacting a compound represented by general formula (II) with a compound represented by general formula (III) in the presence of a transition metal-phosphine complex and a base.

9. The method for producing an optically active diphosphine according to claim 1, wherein said reacting is carried out at a temperature of from 80° to 140° C.

10. The method for producing an optically active diphosphine according to claim 2, wherein said reacting is carried out at a temperature of from 80° to 140° C.

11. The method for producing an optically active diphosphine according to claim 1, wherein said reacting step provides a mixture containing an optically active diphosphine compound represented by general formula (I) and an optically active diphosphinemonoxide compound, and said method further comprises the step of reducing said optically active diphosphinemonoxide compound to an optically active diphosphine compound represented by general formula (I).

12. The method for producing an optically active diphosphine according to claim 2, wherein said reacting step provides a mixture containing an optically active diphosphine compound represented by general formula (I) and an optically active diphosphinemonoxide compound, and said method further comprises the step of reducing said optically active diphosphinemonoxide compound to an optically active diphosphine compound represented by general formula (I).

13. An optically active diphosphine compound having the following general formula (I):

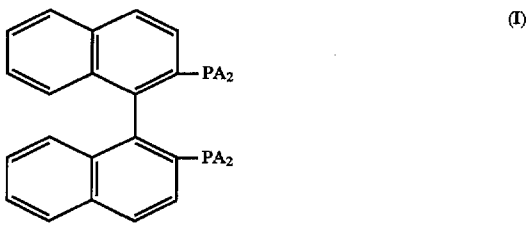

wherein A represents a mono- to tri- substituted phenyl group, wherein each substituent of the substituted phenyl group is selected from the group consisting of a halogen atom, a lower alkyl group, a lower alkoxy group or a lower halogenated-alkoxy group such that the substituents may be the same or different; a naphthyl group; a lower-alkyl naphthyl group; or a lower-alkoxy-naphthyl group.

14. The optically active diphosphine compound according to claim 13, wherein A is a 3,4,5-trimethylphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-fluorophenyl group, a 4-trifluoromethylphenyl group, a 3-trifluoromethylphenyl group, a 4-biphenyl group, a 3-biphenyl group, a 4-dimethylaminophenyl group, an α-naphthyl group, a βD-naphthyl group, a 6-methoxy-α-naphthyl group or a 6-methoxy-β-naphthyl group.

15. An optically active diphosphinemonoxide compound represented by the following general formula (IV):

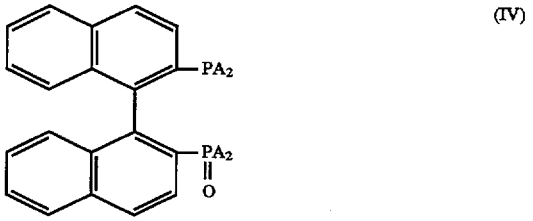

wherein A represents a mono- to tri- substituted phenyl group, wherein each substituent of the substituted phenyl group is selected from the group consisting of a halogen atom, a lower alkyl group, a lower alkoxy group or a lower halogenated-alkoxy group such that the substituents may be the same or different; a naphthyl group; a lower-alkyl naphthyl group; or a lower-alkoxy-naphthyl group.

16. The optically active diphosphinemonoxide compound according to claim 15, wherein A is a 3,4,5-trimethylphenyl group, a 3-methoxyphenyl group, a 3,5-dimethoxyphenyl group, a 3,4,5-trimethoxyphenyl group, a 3,5-dimethyl-4-methoxyphenyl group, a 3,4-methylenedioxyphenyl group, a 4-fluorophenyl group, a 4-trifluoromethylphenyl group, a 3-trifluoromethylphenyl group, a 4-biphenyl group, a 3-biphenyl group, a 4-dimethylaminophenyl group, an α-naphthyl group, a β-naphthyl group, a 6-methoxy-α-naphthyl group or a 6-methoxy-β-naphthyl group.

* * * * *